United States Patent [19]

Yagi

[11] Patent Number: 4,798,538
[45] Date of Patent: Jan. 17, 1989

[54] ABDOMINAL RESPIRATION TRAINING SYSTEM

[75] Inventor: Hiroshi Yagi, Toyama, Japan

[73] Assignee: Elco Co., Ltd., Toyama, Japan

[21] Appl. No.: 53,760

[22] Filed: May 26, 1987

[30] Foreign Application Priority Data

May 27, 1986 [JP] Japan .................. 61-121853

[51] Int. Cl.⁴ .............................. A61B 5/02
[52] U.S. Cl. .................... 434/262; 128/721
[58] Field of Search ............. 434/262; 128/716, 718, 128/719, 721

[56] References Cited

U.S. PATENT DOCUMENTS 4,630,614 12/1986 Atlas .................. 128/721
4,665,926 5/1987 Leuner et al. ............ 128/716

FOREIGN PATENT DOCUMENTS 1492875 11/1977 United Kingdom ........... 128/721

Primary Examiner—Leo P. Picard
Attorney, Agent, or Firm—Wenderoth, Lind & Ponack

[57] ABSTRACT

A training instruction based on an ideal breath pattern to obtain the relaxation state in which the alpha wave mainly appears is informed by the acoustic output and/or photoelectric display in order to perform the respiration training. The state of the abdominal respiration of a person to be examined is detected by a sensor attached to the abdominal region. The detected breath pattern by the abdominal respiration is compared with the ideal breath pattern. A degree of similarity between them is informed.

6 Claims, 6 Drawing Sheets

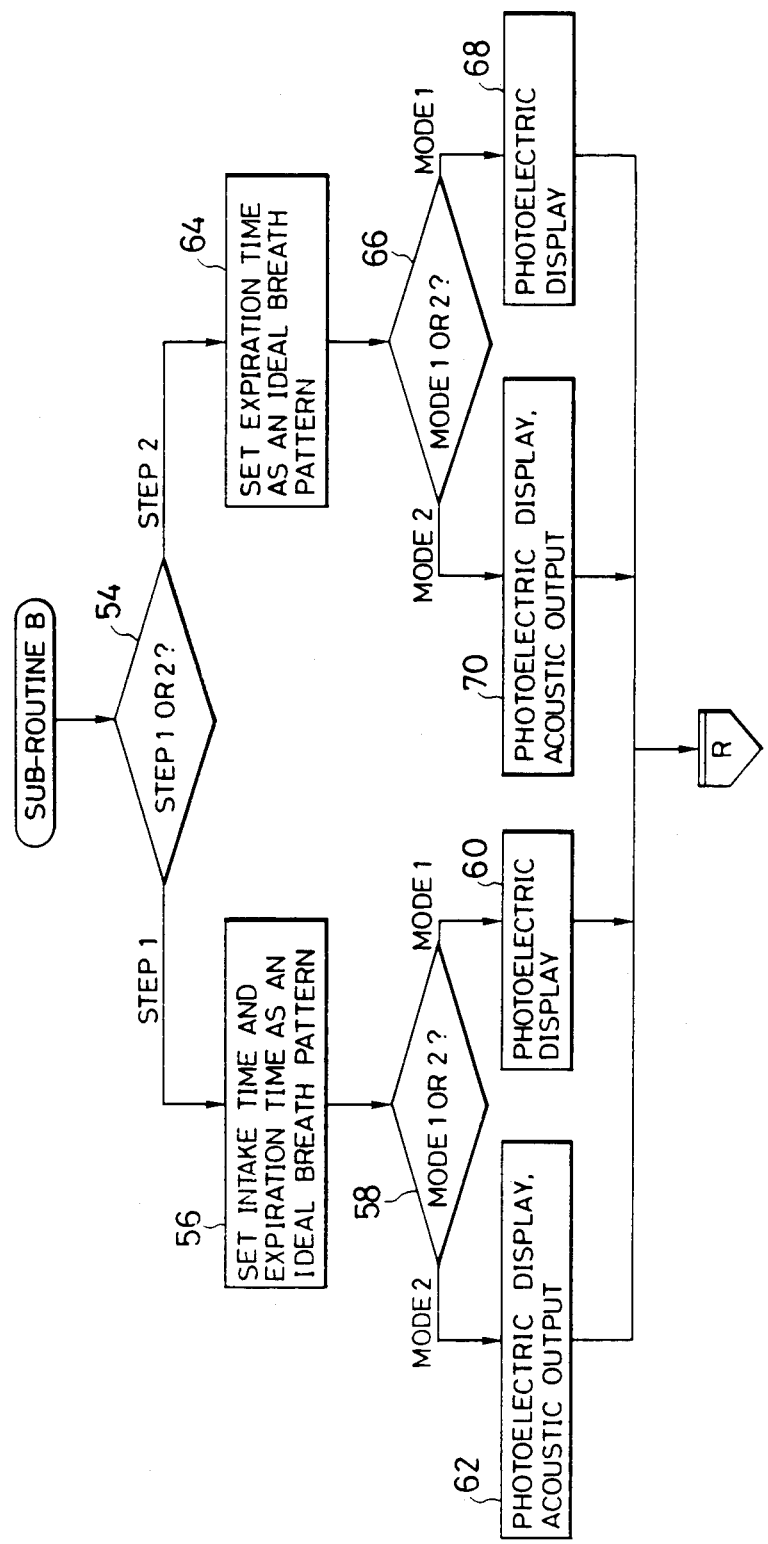

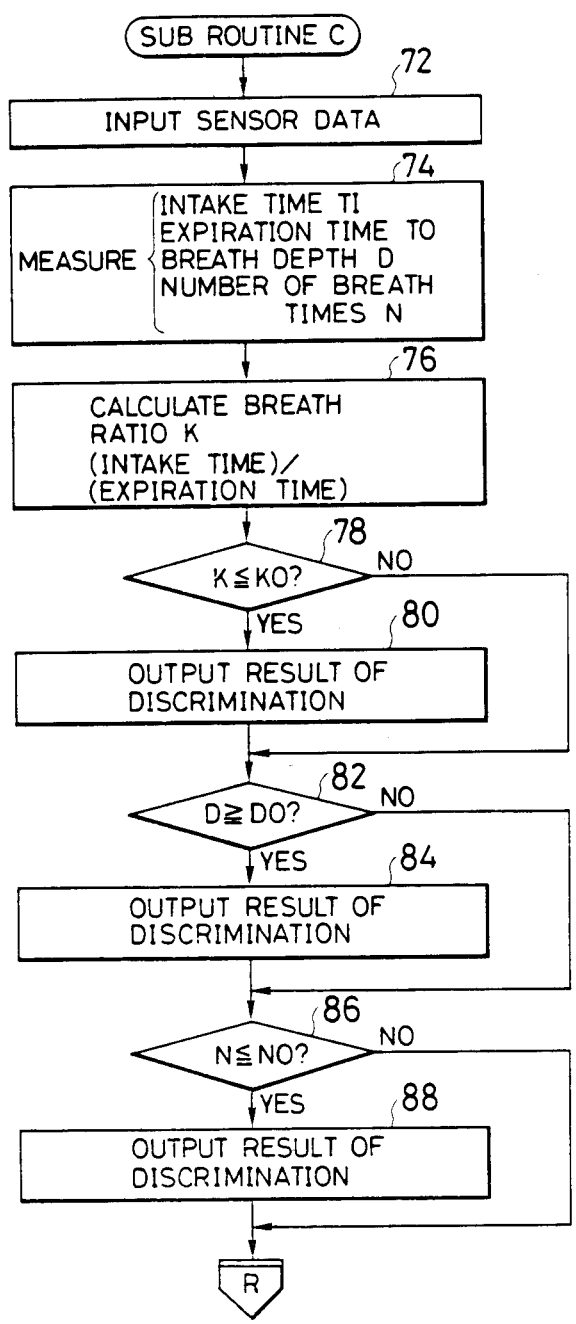

ABDOMINAL RESPIRATION TRAINING SYSTEM

BACKGROUND OF THE INVENTION AND RELATED ART STATEMENT

The present invention relates to an abdominal respiration training system for training a respiration method and, more particularly, to an abdominal respiration training system for use in training of the abdominal respiration to maintain and recover the health.

Hitherto, in Zen, yoga, or the like, the abdominal respiration method has been suggested as the most significant method to obtain the stable state of spirit.

However, the very busy moderns do not have an enough time to perform Zen, yoga, or the like for a long period of time under the proper instruction. The physical and mental stresses are, in many cases, stored because of the busy life. Therefore, if the abdominal respiration method which is applied to Zen, yoga, or the like can be used in the daily life, the mental and physical stresses can be eliminated. For this purpose, it is demanded to realize an abdominal respiration training system which can be easily used at home.

Hitherto, as such a system for training the abdominal respiration method, for example, there has been known a system for allowing a patient having a disease of the respiratory organs or the like to learn the optimum respiration method to the lung.

Namely, when a person to be examined breathes through a mouthpiece or mask, the speed or flow rate of the air passing through the mouthpiece or mask is measured. The result of the measurement is displayed on a CRT display device together with an ideal breath waveform pattern for comparison. The person to be examined performs the respiration training such that his breath waveform pattern approaches the ideal breath waveform pattern.

However, in such a conventional respiration training system, since the person to be examined must use the mouthpiece or mask, it is hard to perform the natural respiration training. In addition, the use of the mouthpiece or mask gives an unpleasant feeling or strain to the person to be examined. Further, since the flowing speed meter or flow meter is needed to measure an amount of breath, the cost of the system increases. On the other hand, since the person to be examined must perform the respiration training while observing the display screen of the CRT display device, there are problems such that he will easily feel tired and cannot perform the respiration training for a long time. Consequently, such a conventional respiration training system is not suitable for training the abdominal respiration at home.

SUMMARY OF THE INVENTION

It is an object of the present invention to provide an abdominal respiration training system which is useful to eliminate the mental and physical stresses.

Another object of the invention is to provide an abdominal respiration training system which can simply and easily train the abdominal respiration in the daily life.

Still another object of the invention is to provide an abdominal respiration training system which can expect the high training effect by use in the daily life.

Still another object of the invention is to provide an abdominal respiration training system in which a predetermined ideal breath training pattern is instructed by the sound and photoelectric display.

Still another object of the invention is to provide an abdominal respiration training system which can freely select a training step and a training level in accordance with a training situation.

Namely, according to the present invention, the motion of the abdominal wall in association with the abdominal respiration is detected by a sensor attached to the abdominal region of a person to be examined. On the other hand, an ideal breath pattern in the abdominal respiration adapted to obtain the relaxation state necessary to eliminate the mental and physical stresses is generated and informed to the person to be examined by an acoustic output and/or photoelectric display. The person to be examined trains the abdominal respiration in accordance with an instruction of the ideal breath pattern informed. The abdominal respiration state of the person to be examined is detected by the sensor. The actual breath pattern detected by the sensor is compared with the ideal breath pattern. A degree of similarity between the actual breath pattern and the ideal breath pattern is informed to the person to be examined by the acoustic output and/or photoelectric display.

Therefore, according to the present invention, since the sensor is attached to the abdominal region, the attachment of the sensor does not, in particular, obstruct the respiration training. On the other hand, since the motion of the abdominal wall is detected, a simple sensor such as strain gauge, mercury resistance meter, or the like can be used as a sensor.

In addition, since the ideal breath pattern is informed to the person to be examined by not only the photoelectric display but also the acoustic output, he can easily change his respiration state according to the ideal breath pattern. Further, since the ideal breath pattern is generated as a sound, the person to be examined can perform the respiration training in the state with half an eye or closed eye in which the stable mental condition can be easily obtained.

Moreover, when the breath pattern of the person to be examined approaches the ideal breath pattern, a degree of similarity between them is informed on the basis of the result of the comparison by the system. Therefore, the person to be examined can perform the abdominal respiration training by himself without receiving any special instruction.

The inventors and the like of the present invention have further studied by paying an attention to the relation between the respiration and the brain waves, so that the following conclusion could be derived from the statistic results with respect to an enhancement in alpha wave adapted to obtain the relaxation state of the spirit.

(1) In order to enhance the alpha wave, the abdominal respiration is better than the thoracic respiration.

(2) In the case of the same abdominal respiration, as the number of respiration times is small and as the motion of the abdominal wall is large, the ratio of generation of the alpha wave increases.

(3) As the respiration ratio defined by (intake time)/(expiration time) is small, the ratio of generation of the alpha wave increases.

The foregoing result of the study regarding the relation between the respiration and the brain waves is effectively used in the ideal breath pattern to instruct for training in the abdominal respiration training system according to the present invention.

The above and other objects, features, and advantages of the present invention will become more apparent from the following detailed description in conjunction with the accompanying drawings.

BRIEF DESCRIPTION OF THE DRAWINGS

FIG. 5 is a flowchart showing a detailed sub-routine for selection of a training step in FIG. 3; and FIG. 6 is a flowchart showing a detailed sub-routine for a data comparing process in FIG. 3.

DETAILED DESCRIPTION OF PREFERRED EMBODIMENTS

Figure 1:
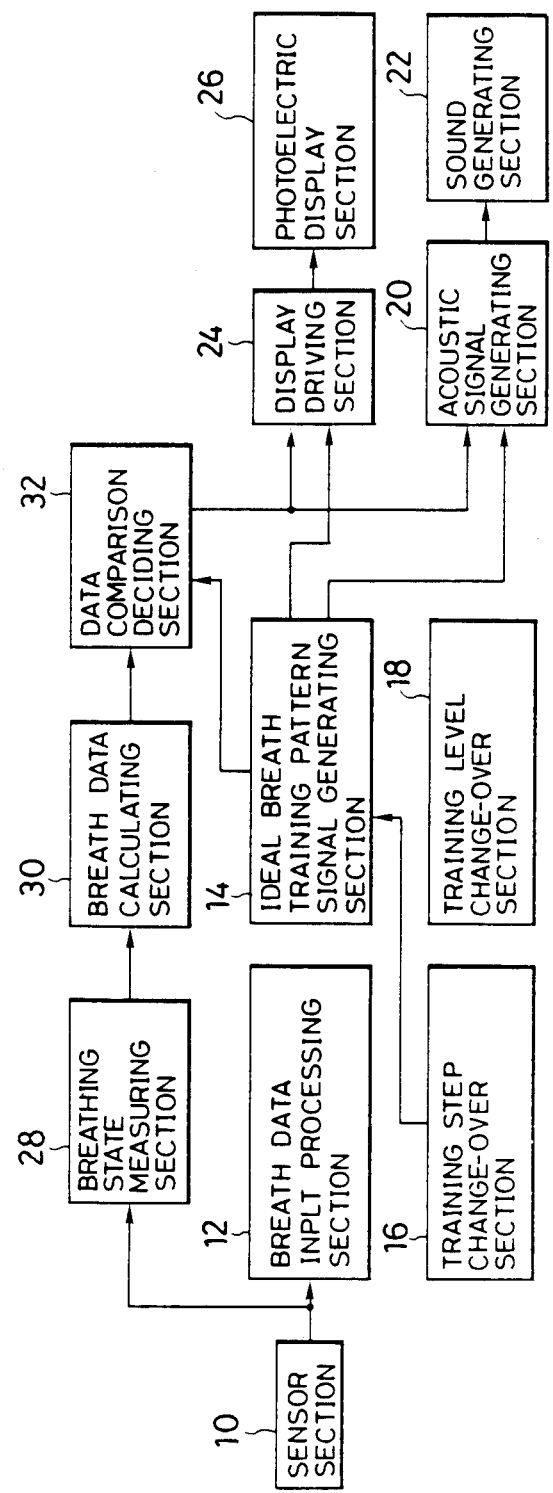
FIG. 1 is a block diagram showing an embodiment of the present invention.

FIG. 1 is a block diagram showing an embodiment of the present invention.

In FIG. 1, a sensor section 10 consists of, for example, a strain gauge, mercury resistance meter, or the like and is attached by a belt or the like to the abdominal region of a person to be examined. The sensor section 10 outputs a signal according to the motion of the abdominal wall in the abdominal respiration of the person to be examined, namely, the inflation state and relaxation state of the abdominal wall in the abdominal respiration.

The detection signal of the sensor section 10 is supplied to a breath data input processing section 12. The detection signal is obtained from the sensor section 10 by the abdominal respiration of the person to be examined prior to training the respiration. On the basis of this detection signal, the processing section 12 detects the maximum value in the inflation state of the abdominal wall when the person to be examined inhaled deepest and the minimum value in the relaxation state of the abdominal wall when he largely exhaled the inhaled air. The processing section 12 stores these maximum and minimum values. The maximum value in the inflation state of the abdominal wall and the minimum value in the relaxation state derived by the breath data input processing section 12 are used to set the maximum and minimum values of the acoustic output and of the photoelectric display by the informing means, which will be explained in detail hereinafter.

An ideal breath training pattern signal generating section 14 generates a signal based on an ideal breath training pattern in a predetermined abdominal respiration training. Practically speaking, the generating section 14 generates time patterns of an ideal intake time $T_i$ and an expiration time $T_0$ to obtain the relaxation state in which the alpha wave is mainly generated in the abdominal respiration. The time patterns are preset on the basis of the respiration ratio, number of respiration times, respiration depth, and the like in the ideal abdominal respiration.

A training step change-over section 16 switches and outputs either one of or both of the intake time $T_i$ and the expiration time $T_0$ as an ideal respiration pattern generated in the generating section 14. The change-over section 16 also has the function to switch the acoustic output and the photoelectric display in the informing means which will be explained in detail hereinafter.

In this embodiment, the training step changeover section 16 can switch the following steps 1 and 2:

(step 1) The intake time and expiration time based on the ideal breath pattern are generated.

(step 2) Only the expiration time is generated.

Further, in each of the steps 1 and 2, modes 1 and 2 can be switched with respect to each of the photoelectric display and the acoustic output in the informing means. When the mode 1 is selected, the ideal breath pattern is informed by only the photoelectric display. On the other hand, when the mode 2 is selected, the ideal breath pattern is informed by the photoelectric display and the acoustic output.

A training level change-over section 18 has the function to select the ideal breath pattern generated from the generating section 14, namely, the time patterns of the ideal intake time and/or ideal expiration time at a plurality of levels in accordance with the degree of training of the person to be examined. For example, five levels can be selected by the training level change-over section 18. The five training levels are set on the basis of the respiration ratio (=intake time/expiration time), respiration depth, and number of respiration times.

For example, in the case of the respiration ratio, as the training degree increases from the level 1 to the level 5, the training level change-over section 18 instructs the ideal breath training pattern signal generating section 14 to generate the time patterns of the ideal intake time and ideal expiration time such that the respiration ratio, which has a value below 1, is set to 0.7, 0.5, 0.3, 0.2, and 0.1. Therefore, a plurality of ideal breath training patterns corresponding to the training levels which can be switched by the training level change-over section 18 are previously stored in the generating section 14.

An acoustic signal generating section 20 generates an acoustic signal on the basis of the pattern signal from the generating section 14. The acoustic signal from the acoustic signal generating section 20 is supplied to a sound generating section 22. A speaker, earphone, headphone, or the like may be used as the sound generating section 22. The acoustic signal generating section 18 receives the pattern signals of the ideal intake time and/or expiration time from the generating section 14 and generates the acoustic signals of the frequencies which are different in dependence on, for example, the intake time and expiration time. In this manner, the intake time and expiration time adapted to give the ideal breath pattern are informed to the person to be examined by the acoustic outputs of the different tones in the sound generating section 22.

A display driving section 24 drives a photoelectric display section 26 on the basis of the pattern signal from the generating section 14. For example, the display section 26 consists of ten display lamps arranged like a bar graph. While the intake time signal is obtained from the generating section 14, the display lamps arranged like a bar graph are sequentially lit on with the elapse of intake time and expiration time. The person to be examined can inhale and exhale with an increase in number of display lamps which were lit on.

Further, the maximum and minimum values of the acoustic output of the sound generating section 22 and of the photoelectric display in the photoelectric display section 26 are specified by the maximum value in the inflation state of the abdominal wall and the minimum value in the relaxation state which were derived by the abdominal respiration of the person to be examined in the breath data input processing section 12 prior to training. For example, in the case of the display by an array of a plurality of display lamps provided in the photoelectric display section 26, the number of lamps to be lit on in the respiration training is determined by the maximum value in the inflation state and the minimum value in the relaxation state which were detected by the processing section 12. Within the range of set number of display lamps, the number of display lamps to be lit on is increased in accordance with the intake time signal and expiration time signal from the generating section 14.

Further, a breathing state measuring section 28 measures the respiration state of the person to be examined on the basis of the detection signal from the sensor section 10. The measuring section 28 measures, for example, the intake time $T_i$, expiration time $T_0$, respiration depth D, and number N of respiration times. The measurement data obtained from the breathing state measuring section 28 is input to a breath data calculating section 30. For example, the calculating section 30 calculates a respiration ratio K ($=T_i/T_0$) on the basis of the intake time $T_i$ and expiration time $T_0$. The respiration depth D and the number N of respiration times are directly output.

The data derived from the calculating section 30 is supplied to a data comparison deciding section 32. The deciding section 32 compares the detection data consisting of the respiration ratio K, respiration depth D, and number N of respiration times from the breath data calculating section 30 with reference values $K_0$, $D_0$, and $N_0$ of the respective data which are given from the ideal breath training pattern signal generating section 14. When the detection data coincides with each reference value, or when the detection data falls within a predetermined range of each reference value, the deciding section 32 determines that the abdominal respiration state of the person to be examined has reached the ideal breath pattern. Thus, the deciding section 32 outputs a coincidence signal to the acoustic signal generating section 20 and display driving section 24. Therefore, the sound generating section 22 and/or photoelectric display section 26 inform the degree of similarity between the actual breath pattern and the ideal breath training pattern.

Figure 2:
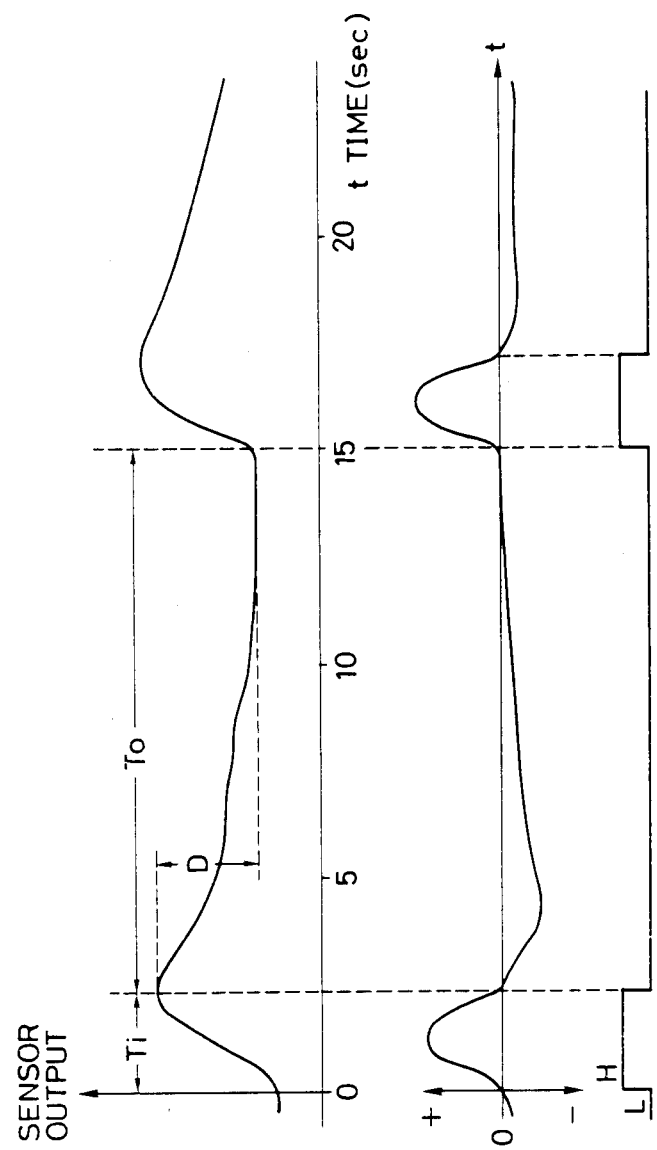
FIG. 2A is a time chart showing a detection signal of a sensor in FIG. 1.
FIG. 2B is a time chart showing a differentiation signal of the detection signal of the sensor in FIG. 1.
FIG. 2C is a time chart showing a gate signal indicative of the intake time and expiration time obtained from the differentiation signal of FIG. 2B.

FIG. 2A shows a detection signal output from the sensor section 10 in FIG. 1 in the abdominal respiration. The breathing state measuring section 28 measures the intake time $T_i$ and expiration time $T_0$ from the detection signal and also measures the respiration depth D from the difference between the maximum value and the minimum value of the detection signal level. In measurement of the intake time $T_i$ and expiration time $T_0$, for example, the detection signal shown in FIG. 2A is differentiated to obtain a differentiation signal shown in FIG. 2B, and the differentiation signal is further converted into a gate signal shown in Fig. 2C by detecting the zero cross point. The intake time $T_i$ is measured by counting clock pulses by a counter when the gate signal of FIG. 2C is at the H level. On the other hand, the expiration time $T_0$ can be measured by counting clock pulses by another counter when the gate signal is at the L level.

The training process of the abdominal respiration according to the embodiment of FIG. 1 will now be described with reference to a flowchart of FIG. 3.

Prior to training, the person to be examined first performs the deep abdominal respiration with a sensor attached to the abdominal region. By the abdominal respiration, the breath data of the person to be examined is input and processed in step 34.

Figure 4:
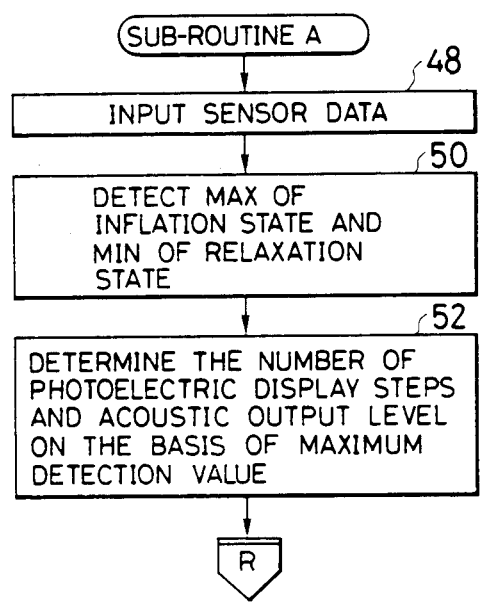
FIG. 4 is a flowchart showing a detailed sub-routine for an input process in FIG. 3.

The details of the input process in step 34 are shown in a sub-routine A in FIG. 4.

In FIG. 4, the detection data of the sensor is first input for a constant time in step 48. In the next step 50, the maximum value in the inflation state and the minimum value in the relaxation state of the abdominal region by the abdominal respiration are detected from the input detection data and stored into a memory. In step 52, the number of display lamps to be lit on in the photoelectric display section 26 and the acoustic output level for the sound generating section 22 are determined on the basis of the maximum and minimum values detected.

Referring again to FIG. 3, after completion of the input process in step 34, the breath training step is selected in step 36. The breath training step is selected by operating the switch in the training step change-over section 16 in FIG. 1. For example, the training step is switched and selected in accordance with, e.g., a sub-routine B in FIG. 5.

In the sub-routine B in FIG. 5, either the step 1 or the step 2 is selected and checked in step 54. For example, the step 1 is selected when the training degree is low. The step 2 is selected as the training degree progresses. When the step 1 is selected, step 56 follows after step 54 and the intake time and expiration time as the ideal breath pattern are set as a pattern output. Further, in selection of the step 1, either the acoustic output mode or the photoelectric display mode is selected. For example, when the mode 1 is selected, step 60 follows after step 56 and the breath pattern is informed by only the photoelectric display. On the other hand, when the mode 2 is selected, step 62 follows after step 58 and the breath pattern is informed by both of the photoelectric display and the acoustic output.

Next, when the training degree advances and the step 2 is selected, step 64 follows after step 54. Only the expiration time is set as an ideal breath pattern. Subsequently, the mode 1 or 2 is selected in step 66 similarly to the case of the step 1. When the mode 1 is selected, step 68 follows and the breath pattern is informed by only the photoelectric display. When the mode 2 is selected, step 70 follows and the breath pattern is informed by both of the photoelectric display and the acoustic output.

Referring again to FIG. 3, after the process to select the breath training step in step 36 was finished, the next step 38 follows and the breath training level is selected by the training level change-over section 18 in FIG. 1. For example, the proper training level can be selected in accordance with the degree of progress of the training.

In the next step 40, the ideal breath pattern is generated on the basis of the training level and training step which were set in steps 36 and 38. Namely, in the step 1, the ideal intake time and expiration time are output. When the step 2 is selected, only the expiration time is output. On the basis of the ideal breath pattern output, the sound generating section 22 and/or photoelectric display section 26 in FIG. 1 inform the ideal intake time and/or ideal expiration time by the acoustic output and photoelectric display. Therefore, when the training step 1 is selected, the person to be examined performs the abdominal respiration in accordance with the photoelectric display of the photoelectric display section 26. When the training step 2 is selected, the person to be examined performs the abdominal respiration training in accordance with not only the photoelectric display but also the intake and expiration acoustic outputs of the sound generating section 22 consisting of a speaker, earphone, or headphone.

When the generation of the ideal breath pattern is started in step 40, the process to compare the breath data of the person to be examined with the ideal breath pattern is performed in the next step 42. The process to compare and decide the breath data in step 42 is shown in a sub-routine C in FIG. 6.

Namely, the detection data of the sensor is input in step 72. In the next step 74, the intake time $T_i$, expiration time $T_0$, respiration depth D, and number N of respiration times in the abdominal respiration of the person to be examined are measured on the basis of the detection data of the sensor. In the next step 76, the respiration ratio K is calculated on the basis of the intake time $T_i$ and expiration time $T_0$ measured. Then, the respiration ratio K calculated in step 76 is compared with the preset reference value $K_0$ in step 78. The reference value $K_0$ is set to a proper value below 1. When the respiration ratio K is below the reference value $K_0$, step 80 follows and the result of the decision indicating that the actual breath pattern has reached the ideal breath pattern is output, thereby allowing the photoelectric display or acoustic output to be performed on the basis of this decision output.

In the next step 82, the respiration depth D is compared with the reference value $D_0$. When the respiration depth D is above the reference value $D_0$, step 84 follows and the result of the decision indicating that the respiration depth has reached the depth to give the ideal breath pattern is output, thereby allowing the acoustic output or photoelectric display to be executed on the basis of this decision output. Further, in step 86, the number N of respiration times is compared with the reference value $N_0$. When the number N is below the reference value $N_0$, step 88 follows and the result of the decision indicating that the number of respiration times has reached the value to give the ideal breath pattern is output, thereby allowing the acoustic output or photoelectric display to be similarly performed to inform the person to be examined.

Each of the reference values $K_0$, $D_0$, and $N_0$ in the discriminating steps 78, 82, and 86 in FIG. 6 is set to a different value in accordance with the level selected in the training level change-over section 18 shown in FIG. 1. For example, the reference value $K_0$ of the respiration ratio is set to a value below 1 which sequentially decreases as the training level increases. The reference value $D_0$ of the respiration depth is set to a value which increases as the training level rises. The reference value $N_0$ of the number of respiration times is set to a value which decreases as the training level increases.

Figure 3:
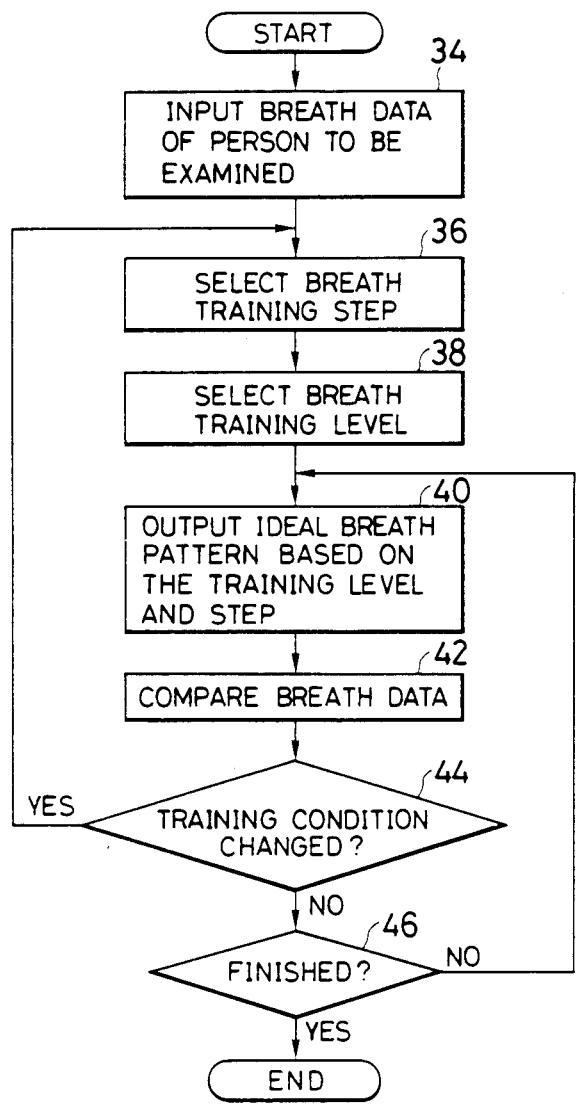
FIG. 3 is a flowchart showing a main routine for a training process according to the invention.

Referring now to FIG. 3, after completion of the process to compare the breath data in step 42, step 44 follows and a check is made to see if the training condition has been changed or not. If the training step or training level has been changed, the processing routine is returned to step 36 and a new ideal breath pattern based on the change in the training condition is output. If the training condition is not changed, step 46 follows and a check is made to see if the training has been finished or not. The processes in steps 40 to 46 are repeated until the training is finished.

In the embodiment, the person to be examined can freely switch the training level and training step. The invention can be also applied to another embodiment such that the training step and training level are automatically switched from the low degree to the high degree with an elapse of the training time.

In the embodiment, the training steps are all selected by the discrimination by the person to be examined. However, the training program can be also optimized by the following manner. For example, until a certain time after the start of the training, the acoustic output and/or only the photoelectric display are performed on the basis of the ideal breath training pattern and the result of the comparison of the breath data of the person to be examined with the ideal breath pattern is not generated. After a predetermined training time has elapsed, the transfer of the ideal breath training pattern is stopped and the person to be examined performs the training by himself. Only in this case, the result of comparison of his breath data is output. In this manner, the training steps are set.

Further, it is also possible to forcedly inform only the ideal breath training pattern to the person to be examined without informing the result of the training to the person to be examined. In this case, it is possible to omit the breathing state measuring section 28, breath data calculating section 30, and data comparison deciding section 32 in FIG. 1.

Further, the respiration ratio in the data calculating section may be calculated as a value above 1 on the basis of (expiration time/intake time).

What is claimed is:

1. An abdominal respiration training system comprising:
    a sensor which is attached to an abdominal region of a person to be examined and detects the motion of the abdominal wall by an abdominal respiration;
    a training pattern generating means for generating an ideal pattern of an inspiration time and/or an expiration time on the basis of ideal values of a respiration ratio, a respiration depth, and a number of respiration times, so as to obtain a relaxation state in which an alpha wave mainly appears;
    a breath pattern calculating means for calculating an actual breath pattern of the person to be examined from a detection signal of said sensor;
    a comparison deciding means for comparing the pattern calculated by said breath pattern calculating means with the ideal breath training pattern from said training pattern generating means, and for deciding a degree of similarity between said calculated pattern and said ideal breath training pattern; and
    an informing means for informing said ideal breath training pattern and an output of said decision indicative of the degree of similarity to the person to be examined by an acoustic output and/or photoelectric display.

2. A system according to claim 1, wherein said training pattern generating means has a training step change-over means for switching a first training pattern to instruct the ideal intake time and ideal expiration time and an second training pattern to instruct only the ideal expiration time and for outputting the selected training pattern.

3. A system according to claim 1, wherein said training pattern generating means has a training level change-over means for generating the breath training pattern which differs in dependence on the switching of the set training level.

4. A system according to claim 1, wherein said training pattern setting means has a change-over means for switching and selecting either one of or both of the photoelectric display and the acoustic output of the training pattern by said informing means.

5. A system according to claim 1, wherein said training pattern generating means has:
a memory means for detecting the maximum value of the inflation state of the abdominal wall and the minimum value in the relaxation state of the abdominal wall by the abdominal respiration from the detection signal of said sensor which was derived prior to starting of the training and for storing said maximum and minimum values; and
a means for setting the maximum value and the minimum value of each of the acoustic output and the photoelectric display in said informing means on the basis of the maximum value and the minimum value which were stored in said memory means.

6. A system according to claim 1, wherein said breath pattern calculating means has means for calculating a respiration ratio, a respiration depth, and a number of respiration times from the detection signal of said sensor.

* * * * *